(12) United States Patent
Wehrli

(10) Patent No.: US 8,197,862 B2
(45) Date of Patent: Jun. 12, 2012

(54) METHOD OF MAKING DISTILLED OLIVE JUICE EXTRACTS

(75) Inventor: Christof Wehrli, Witterswil (CH)

(73) Assignee: DSM IP Assets B.V., Heerlen (NL)

( * ) Notice: Subject to any disclaimer, the term of this patent is extended or adjusted under 35 U.S.C. 154(b) by 237 days.

(21) Appl. No.: 12/674,034

(22) PCT Filed: Aug. 19, 2008

(86) PCT No.: PCT/EP2008/006789
§ 371 (c)(1),
(2), (4) Date: Feb. 18, 2010

(87) PCT Pub. No.: WO2009/024317
PCT Pub. Date: Feb. 26, 2009

(65) Prior Publication Data
US 2011/0129556 A1    Jun. 2, 2011

(30) Foreign Application Priority Data
Aug. 21, 2007 (EP) ..................................... 07016343

(51) Int. Cl.
*A01N 65/00* (2009.01)

(52) U.S. Cl. ........................................................ 424/725
(58) Field of Classification Search ........................ None
See application file for complete search history.

(56) References Cited

U.S. PATENT DOCUMENTS
2008/0014322 A1   1/2008   Ibarra et al.

FOREIGN PATENT DOCUMENTS
| EP | 1 462 013 | 9/2004 |
| EP | 1 582 512 | 10/2005 |
| EP | 1 980 706 | 10/2008 |

OTHER PUBLICATIONS

International Search Report for PCT/EP2008/006789, mailed Jan. 5, 2009.
Written Opinion of the International Searching Authority for PCT/EP2008/006789, mailed Jan. 5, 2009.

*Primary Examiner* — Michael Meller
(74) *Attorney, Agent, or Firm* — Nixon & Vanderhye P.C.

(57) ABSTRACT

In accordance with this invention, new processes for making an all-natural, hydroxytyrosol-rich, non bitter olive juice extract and its distillate is presented. Also as part of this invention are novel juice extract distillate and compositions containing this novel olive juice extract distillate.

7 Claims, No Drawings

METHOD OF MAKING DISTILLED OLIVE JUICE EXTRACTS

This application is the U.S. national phase of International Application No. PCT/EP2008/006789 filed 19 Aug. 2008, which designated the U.S. and claims priority to Europe Application No. 07016343.1 filed 21 Aug. 2007, the entire contents of each of which are hereby incorporated by reference.

FIELD OF THE INVENTION

This invention relates to distilled olive juice extracts, and to methods of making these extracts. Olive juice extracts can be used as nutritional supplements, as they have potent antioxidant activities. Nutritional compositions containing these novel extracts are also part of this invention.

BACKGROUND OF THE INVENTION

The medicinal benefits of olive oil and olive extracts is widely being recognized. To make olive oil, the olive fruits are ground into a paste. Pressure is applied to the paste to separate the oil from the ground fruit. In addition to providing olive oil, the pressing also releases the water content of the olive fruit, which contains many water soluble phytochemicals. This water is known by a number of names, including "vegetation water", "olive juice", and "olive waste water". Interestingly, while olive juice and its disposal can be a problem for the olive oil producer, this olive juice can be a desirable rich source of phenolic compounds, which can have beneficial nutritional properties.

In the past, methods to concentrate the nutritional olive juice involved time consuming incubation, filtration and/or centrifugation, and/or spray drying steps. Another problem is that the usability of dried or liquid olive juice in food or dietary supplements is limited due to the smell, bitterness, and turbidity of the olive juice, as well as the low content of hydroxytyrosol, one of the active polyphenols.

It would therefore be desirable to develop a better method for producing an all-natural, hydroxytyrosol-rich, non-bitter olive juice extract which is efficient and cost-effective.

DESCRIPTION OF THE INVENTION

In accordance with this invention, new processes for making an all-natural, hydroxytyrosol-rich, non bitter olive juice extract distillate is presented. Also as part of this invention are novel juice extract distillate and compositions containing this novel olive juice extract distillate.

A typical olive will contain approximately 50% water, 22% oil, 19% carbohydrates, 6% cellulose, 2% proteins, and oleuropein and hydroxytyrosol (combined) 0.2%. It should be appreciated that the exact makeup of the fruit (and its subsequent extract) will vary according to the variety of olive used, the time of harvest, and even growing conditions.

Contrary to literature reports (see e.g., Briante et al, 2002, *J. Biotechn.* 93: 109-119, and Soler-Rivas et al 2000, *J Sci Food Agric* 80:1013-1023) it has been found, in accordance with this invention, that the unknown compounds which impart a bitter taste to the olive juice are neither hydroxytyrosol nor oleuropein. While not wishing to be bound by theory, they may contain a labile phenolic ester group. Regardless of the identity of the bitter compounds, they are very sensitive to base, and are not stable at higher pH.

As used throughout the specification and claims, the following definitions apply:

"HT" means hydroxytyrosol.

"Olive Juice", "Olive Waste Water" and "Vegetation Water" are terms all intended to be used interchangeably. They refer to the water phase produced during olive oil production. It is a slurry with a complex mixture of carbohydrates along with the compounds of interest, such as HT and oleuropein (which contains bound HT, and which may be subsequently broken down to yield HT).

Thus, one aspect of this invention is a method of producing a hydroxytyrosol rich olive juice comprising:

a) obtaining a hydroxytyrosol enriched olive juice concentrate which is clear, solids-reduced, triglycerides-reduced, and fatty acids-reduced; and b) distilling the hydroxytyrosol extract from step a) to form an olive juice distillate.

Another aspect of this invention is a method of producing a hydroxytyrosol rich olive juice distillate comprising: a) obtaining an olive juice extract wherein the amount of solids, triglycerides, fatty acids are substantially reduced compared to untreated olive juice; and b) extracting the olive juice extract with a water-immiscible solvent to obtain a hydroxytyrosol extract; and c) distilling the hydroxytyrosol extract to form the olive juice distillate.

If triglycerides, free fatty acids or other esters (like olive oil, oleic acid and oleic acid ethylester) are present in the olive juice then they should be reduced or removed completely before a juice is distilled to avoid contamination of distilled HT. Fatty acids and esters are not soluble in HT, but will form a turbid or 2-phase distillate, as fatty acids and simple esters (like oleic acid and oleic ethyl ester) distill together with HT.

Forming a Triglyceride, Fatty Acid, Oleic Acid Ethyl Ester-Reduced Distilling Material There are two main typical commercially available forms of olive juice which can be used in this processes of this invention. The first is fresh olive juice. This may be simply obtained in an untreated state from the originator (typically an olive oil producer), or it may have undergone procedures such as centrifugation or filtration to remove solids and triglycerides. A second form which can be used in this invention after re-hydration, is a spray dried or freeze dried form which may have been stabilized with citric acid. Any source is acceptable for distilling, after treatments as described below. Typically the starting juice may have solids, fats (oils) and/or fibers present in it, or after pretreatment like centrifugation or ultrafiltration is free of solids and triglycerides or fatty acids. Also appropriate is olive juice which is purchased in concentrated form, or concentrated prior to use by standard techniques known in the art.

If needed, fibers and/or part of the non-volatiles can be removed by ethanol precipitation, as described in co-filed U.S. patent application Ser. No. 12/674,044, and summarized here.

Typically unprocessed olive juice will contain a large amount of fine fibers. These are difficult to filter out as they tend to clog membrane filters, requiring a large amount of maintenance. The fibers, residual oil and lipids, and/or other solids present in the olive juice can be agglomerated and then easily reduced by a) adding a solvent in an amount (by volume) equal to about 40-400% of the olive juice or partially concentrated olive juice to form two phases; and then b) separating the two phases.

The solvent which can be employed in this process can be any solvent or mixture of solvents which is water-miscible or nearly miscible like n-butanol. Alcohols, especially C1 to C4 (or mixtures thereof) are preferred, and ethanol is particularly preferred, especially when the end product is to be used in food or as part of a medicinal or nutritional supplement product. Other solvents which can also be utilized include: acetonitrile and acetone.

The amount of solvent is not especially critical, and will depend on the amount of water in the mixture. Usually the solvent will be needed in an amount that is at least equal to the amount of water present. so for example, if ethanol is the solvent, for every 500 ml of water, about 600 ml of EtOH will be required. However, this is subject to a wide range: from about 40-400% solvent compared to the amount of water by weight, preferably 100-240%, and more preferably about 160-220% solvent compared to the amount of water. The important criteria is that enough solvent is added so that two distinct phases are formed.

The temperature of this step is not particularly critical and may range from 0 degrees Celsius to about 80 degrees Celsius, or any temperature which is less than the boiling point of the mixture. Conveniently the temperature will be between about 20 and 60 degrees C., and most conveniently is room temperature, or about 25 degrees.

At this point, two phases exist and any convenient means can be used to separate the two phases. The method of separation will depend on the actual make up of the material. For some batches, a filter can now be easily used, and/or a centrifuge. Other batches could be easily processed by simple decantation or ordinary phase separation.

The solvent can be recovered for re-use, if desired, making the process more economical. Evaporation is generally the easiest way to recover the solvent.

The resulting product is a solids-, triglycerides-, fatty acids- (e.g. oleic acid) and fatty acid ethylester (e.g. oleic acid ethylester)-reduced olive juice extract which can be used as the starting material for the next step of this invention. By reduced, it is meant that the amount of solids, triglycerides, fatty acids and oleic acid esters remaining in the extract are substantially reduced, and approaching undetectable. If necessary the triglycerides, fatty acids, and oleic acid ethylesters can be further reduced by extraction with n hexane, or by centrigugation and/or decantation. For optimal results, it is preferred that the amount of these components be a low as possible (less than about 1%). In particularly preferred embodiments, the olive juice extract is solids-free, triglycerides-free, fatty acids-free and fatty acid ethylester-free.

Extraction of HT

In accordance with this invention it has been found that hydroxytyrosol can be extracted from a clear, solids-, triglycerides-, fatty acid-, oleic acid ethylester-reduced olive juice extract such as that resulting from the above steps, by using a water-immiscible solvent such as ethylacetate, methylacetate, butylacetate, and THF. For most applications, including those where the end-product is intended to be used as a nutritional or a pharmaceutical product, ethylacetate, and especially food-grade ethylacetate is preferred.

It is preferred to extract at a higher pH (such as 8-9) to increase the content of hydroxytyrosol in the extracts, but any pH ranging from about 3-11 can be used. Hydrolysis at pH greater than about 9 also forms some free oleic acid, which can be extracted by n-hexane at slightly acidic pH (approximately 6 or below), if required.

The extraction may need to be repeated several times for optimum results or can be performed in a multistep extraction column, due to the relatively low partition coefficient (EtOAc/water is approximately 1). Despite this extraction coefficient of HT being independent of the pH (at pH 4 to 8), the extraction is more efficient at pH equal to or above approximately 7; since at a lower pH substantial amounts of unknown compounds, are also extracted, thereby lowering the purity of HT in the extract.

The extract so obtained from the extraction step makes up yet another aspect of this invention. The extract is clear, has a reduced amount of solids, a reduced amount of trigylcerides, a reduced amount of fatty acids, compared to the starting olive juice. Preferably, the "reduced amounts" are quite low, i.e. are present in an amount which is less than 10% of what was present in the starting juice, and more preferably, are approaching undetectable.

In an alternative step, instead of extracting HT from the clear, solids-, triglycerides-, fatty acids-oleic acid ethylester-reduced olive juice extract can be concentrated using and adsorption process. Hydroxytyrosol can be enriched by adsorbtion on resins, instead of extracting hydroxytyrosol with solvents in a process as it has been described in e.g. EP 2172429, WO02/064537. In this process, a chromatographic treatment is preferred using a neutral resin, preferably an AMBERLYST XAD or similar type resin.

Distilling the HT Extract

The resulting HT-enriched extract resulting from either of the above processes can now be distilled using a conventional or preferred a short path distilling apparatus. If the olive juice has a lower concentration of HT (i.e. less than about 10%), then distillation is not possible, as either the HT could not be distilled, or it underwent decomposition, despite the reported distillation of pure HT (Baralda et al 1983 *Liebigs Ann. Chem.* 684-686).

In accordance with this invention it has been surprisingly found that after extraction, the enriched extract containing at least about 30% HT can be distilled to obtain an even higher concentration distillate in high yields (greater than about 60%).

In a preferred embodiment the distillation takes place in a vacuum at about <2 mbar. The resulting distillate, which forms yet another aspect of this invention is a nearly colorless highly viscous liquid containing approximately 50-85% HT, and 8-15% tyrosol.

If desired, the tyrosol can be removed almost completely by subjecting the distillate to a second fractionated distillation. Thus another aspect of this invention is re-distilling the previously obtained distillate to produce a re-distillate with a ratio of hydroxytyrosol to tyrosol of from 10:1 to >50:1.

The distillates of this invention (i.e. that produced after a first distillation, and that produced after a second distillation) can be a component of a nutritional item for either humans or animals by using in combination with conventional feeds, foods or beverages. Additionally, the distillates may be formulated, using conventional methods into pharmaceuticals, such as tablets, capsules, liquids, and the like. Alternatively, they can be used as part of a cosmetic composition.

The invention is now further illustrated in the following non-limiting examples.

EXAMPLES

Example 1

Starting Material

Unless otherwise stated, all % s given refer to weight percent.

Starting material was HIDROX 6% (from CreAgri, Haywood, Calif. Lot 6022406002. This is freeze-dried olive juice which has been stabilized with citric acid. Its content is: (in weight %):

| | |
|---|---|
| Carbohydrates | Approx. 60% |
| Lipids (olive oil) | Approx. 15% |
| Fibers | Approx. 10% |
| Hydroxytyrosol | 2.1% |
| Water | Approx. 2% |

Appearance:

| | |
|---|---|
| Solubility in water: | turbid, fine suspension |
| Taste | bitter |
| Color | beige-brown powder |

Example 2

100 g HIDROX (6% polyphenols) from CreAgri (Example 1) and 80 ml water were added to a reaction flask with a nitrogen atmosphere. The mixture was warmed up to 80° C. and adjusted to pH 9.0, followed by stirring for 30 minutes at 80° C. at pH 9.0 with continuous addition of a total of 38 ml sodium hydroxide 10 mol/l to maintain pH. The suspension was cooled to 60° C. The content of hydroxytyrosol was increased by the base treatment to approximately 130%.

The solids and precipitables where precipitated at 60° C. by addition of 200 g ethanol. The mixture was cooled, stirred at ambient for 30 minutes and filtered by a Buchner funnel. The filter cake was washed with 50 g ethanol 70%/water 30%. The filtrate was adjusted to pH 5 with approximately 5 ml hydrochloric acid 10 mol/l and evaporated at the rotavapor (20 mbar, 60° C.) to recover the ethanol, the non volatile residue 33.5 g. Content [w %]: 7.4% hydroxytyrosol, 0.8% tyrosol. Yield: 119% of the initial hydroxytyrosol.

The residue (33.5 g) was solubilised in 32 ml water. Traces of fatty acids and oils where extracted with 100 ml n-hexane. The water phase was adjusted to pH 8.0 with approximately 4 ml sodium hydroxide 10 mol/l, and extracted with 5×100 ml ethylacetate. The organic phases where successively washed with 10 ml water. The ethylacetate solutions where combined and evaporated to leave: 3.29 g hydroxytyrosol. Content [w %]: 66.0% hydroxytyrosol, 8.3% tyrosol. Yield: 103% of the initial hydroxytyrosol.

2.97 g of the extracted hydroxytyrosol was distilled in a short path distillation apparatus at 0.02-0.2 mbar to yield: 2.38 g Hydroxytyrosol. Content [w %]: 80.1% hydroxytyrosol, 9.7% tyrosol. Yield: 101% of the initial hydroxytyrosol.

Example 3

19.7 g Hydroxytyrosol (content: 70% hydroxytyrosol, 11% tyrosol) of the short path distillation where fractionated distilled in the vacuum (0.02-0.2 mbar) through a column to yield 9.6 g hydroxytyrosol with a content of 86% hydroxytyrosol, 2.6% tyrosol.

Example 4

A concentrated olive juice sample which had fibers removed was obtained (content=0.89% hydroxytyrosol). 243 g was further concentrated in the vacuum to 190 g (contained approx. 50% nonvolatiles). In a reaction flask under an atmosphere of nitrogen the mixture was warmed up to 80° C. and adjusted to pH 8.0 followed by stirring for 30 minutes at 80° C. at pH 8.0 with continuous addition of a total of 32 ml sodium hydroxide 10 mol/l to maintain pH.

To the dark colored mixture was added 280 g ethanol to make the precipitate. The mixture was cooled and stirred at ambient for 1 h. The upper solution was decanted from the precipitate and evaporated at the rotavapor to recover the ethanol. The nonvolatile residue was 78 g. Content [w %]: 2.6% hydroxytyrosol, 0.6% tyrosol. Yield: 93% of the initial hydroxytyrosol.

The residue (78 g) was solubilised in 77 ml water and extracted with 5×100 ml ethylacetate. The organic phases where successively washed with 10 ml water. The ethylacetate solutions were combined and evaporated to leave: 4.0 g hydroxytyrosol. Content [w %]: 40.3% hydroxytyrosol, 9.4% tyrosol. Yield: 74% of the initial hydroxytyrosol.

3.6 g of the extracted hydroxytyrosol was distilled in a short path distillation apparatus at 0.02-0.2 mbar, to yield: 3.0 g Hydroxytyrosol. Content [w %]: 41% hydroxytyrosol, 14.6% tyrosol. Yield: 63% of the initial hydroxytyrosol

What is claimed is:

1. A method of producing a hydroxytyrosol rich olive juice distillate comprising:
    a) extracting an olive juice extract which contains a reduced amount of solids, carbohydrates, triglycerides and fatty acids as compared to fresh olive juice, with at least one water-immiscible solvent selected from the group consisting of ethylacetate, methylacetate and butylacetate to obtain a hydroxytyrosol enriched olive juice concentrate which is clear, solids-reduced, triglycerides-reduced, and fatty acids-reduced;
    b) removing at least some of the water-immiscible solvent from the hydroxytyrosol enriched olive juice concentrate obtained according to step a); and
    c) distilling the hydroxytyrosol extract from step b) to form an olive juice distillate.

2. A method according to claim 1, wherein the extracting step a) further comprises adjusting the pH of the olive juice extract from about 3 to about 11.

3. A method according to claim 2, wherein the pH is adjusted from about 5 to about 10.

4. A method according to claim 3, wherein the pH is adjusted from about 7 to about 9.

5. A method according to claim 1, wherein the solvent is ethylacetate.

6. A method according to claim 5, wherein step b) comprises removing at least some of the ethylacetate from the hydroxytyrosol enriched olive juice concentrate and recovering the ethylacetate prior to the distilling step c).

7. A method according to claim 1, further comprising:
    d) re-distilling the distillate from step c) to produce a re-distillate with a ratio of hydroxytyrosol to tyrosol of from about 10:1 to >50:1.

* * * * *